United States Patent [19]

Guse et al.

[11] Patent Number: 4,776,850
[45] Date of Patent: Oct. 11, 1988

[54] NITRATE-CONTAINING PLASTER

[75] Inventors: Günter Guse, Hamburg; Bodo Asmussen, Ammerbek; Johannes Böss; Günter Borchert, both of Hamburg, all of Fed. Rep. of Germany

[73] Assignee: Beiersdorf Aktiengesellschaft, Hamburg, Fed. Rep. of Germany

[21] Appl. No.: 862,070

[22] Filed: May 12, 1986

[30] Foreign Application Priority Data

May 24, 1985 [DE] Fed. Rep. of Germany ....... 3518707

[51] Int. Cl.$^4$ ............................................. A61F 13/00
[52] U.S. Cl. .................................... 604/304; 128/156; 424/485; 424/486
[58] Field of Search ................................ 604/304–307, 604/896, 897; 128/156; 424/15–22

[56] References Cited

U.S. PATENT DOCUMENTS

| 3,742,951 | 7/1973 | Zaffarari | 604/307 |
| 3,797,494 | 3/1974 | Zaffaroni | 604/897 |
| 3,964,482 | 6/1976 | Gerstel et al. | 604/896 |
| 4,201,211 | 5/1980 | Chardrasekavan | 604/897 |
| 4,286,592 | 9/1981 | Chardrasekavan et al. | 604/897 |
| 4,291,015 | 9/1981 | Keith et al. | 604/896 |
| 4,314,557 | 2/1982 | Chardrasekavan | 604/307 |
| 4,421,737 | 12/1983 | Ito et al. | 604/897 |

*Primary Examiner*—Stephen C. Pellegrino
*Assistant Examiner*—Mark F. Colosimo
*Attorney, Agent, or Firm*—Sprung Horn Kramer & Woods

[57] ABSTRACT

A self-adhesive plaster with glycerol trinitrate in a self-adhesive composition of a saturated rubber and a tackifying resin for transdermal administration is characterized in that the saturated rubber comprises a higher-molecular, structure-forming component and a low-molecular, plasticizing component.

15 Claims, 1 Drawing Sheet

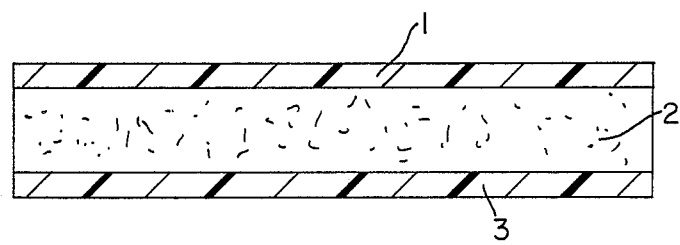

NITRATE-CONTAINING PLASTER

The invention relates to a self-adhesive plaster with glycerol trinitrate in a self-adhesive composition of a saturated rubber and a tackifying resin for transdermal administration.

Such self-adhesive plasters with transdermal administration of glycerol trinitrate are known and also commercially available. Amongst these known plasters, a distinction can be made between two types of plasters and also a mixed type which can be derived from these two.

One known plaster type is characterized by a control membrane which regulates the release of a dose of glycerol trinitrate into the skin. Regarding this type, there is a large number of publications and patents or patent applications, for instance German Patent Specification No. 2,135,533 and U.S. Pat. No. 3,598,122 and 3,797,494. The complicated structure, consisting of a control membrane and the reservoir of active compound provided thereon, limits the applicability of these plasters.

The second type of the known plasters contains the glycerol trinitrate in a more or less adhesive composition which is to be applied directly to the skin, that is to say without a control membrane. Regarding this type, there are again diverse publications and patent applications, for example European Published Application No. 54,279. This type has not been able to gain importance in practice, in particular because of inadequate release of active compound over a prolonged period and the associated unreliable therapeutic effectiveness of such plasters.

As a result of these drawbacks, a mixed type of the two abovementioned plaster types has also already been described. Thus, German Offenlegungsschrift No. 3,315,272 relates, on the one hand, to a glycerol trinitrate plaster of the first type, wherein a pressure-sensitive adhesive layer fulfills the function of the permeable control membrane, behind which a reservoir of layers of different concentrations is located. However, this German Offenlegungsschrift also describes an embodiment in which the pressure-sensitive adhesive composition also contains glycerol trinitrate, as also in Example 1. The self-adhesive composition here consists of a saturated rubber, namely polyisobutylene having a mean molecular weight of 900,000 to 1.4 million. In spite of the concentration gradient of the various layers of the composition, such a plaster cannot really be satisfactory under the conditions in practice. In particular, the plasma concentrations of glycerol trinitrate fall to subtherapeutic values after more than 12 hours.

It was the object of the invention to remedy this situation and in particular to provide a self-adhesive plaster with glycerol trinitrate, which plaster, on the one hand, is of simple structure and can thus be produced economically and which, on the other hand, allows glycerol trinitrate levels in the blood, which are therapeutically adequate over prolonged periods.

Accordingly, the invention relates to a self-adhesive plaster with glycerol trinitrate, such as it is characterized in the patent claims.

Due to the advantageous interaction of the higher-molecular, structure-forming component of the saturated rubber together with the low-molecular, plasticizing component of the saturated rubber, this plaster makes possible, on the one hand, the extremely simple structure of the plaster according to the invention and hence outstandingly economical production thereof, but on the other hand an exceedingly favourable release of the glycerol trinitrate over a prolonged period, the result being superior blood levels. The low-molecular component of the saturated rubber here at the same time fulfills plasticizing functions and promotes the tackiness of the self-adhesive composition prepared from it. In view of the complicated and expensively structured plasters of the state of the art, this represents a surprising solution of the problem in an economically convincing and therapeutically highly effective manner. As a result, the plasters according to the invention are outstandingly suitable for the prophylaxis of angina pectoris or for a use already covered by the glycerol trinitrate plasters commercially available hitherto.

Advantageous molecular weights, quantity ranges, percentages and other preferred embodiments of the plasters according to the invention are to be found in the subclaims.

Techniques known per se can be used for making the plasters according to the invention. Thus, rubber/resin mixtures with solvents can be prepared in a kneader and, for example, saturated hydrocarbon resins can be used as the resins. The active compound formulation is advantageously added to the polymer solutions by means of a further mixing process. It is also possible first to mix the active compound formulation, the resin and a part of the solvent separately and only then to combine them with the prepared rubber solution.

The self-adhesive compositions containing the active compound can be coated directly on the carrier film—which may have been metallized, varnished and precoated—in one or more coats, depending on the type of the desired drying process. To facilitate drying, the composition can in particular be applied in two or three coats. It is also possible, however, to produce the layer or a part layer on an auxiliary support and then to laminate it to the carrier film.

Individual plasters can then be punched out of the coated and dried web, covered with a peel-off protective film and packaged in a sealed sachet.

The invention is explained below by way of example and with reference to the appended drawing, but it is not intended unnecessarily to restrict its subject thereby.

The FIGURE is the sectional view of the plaster according to the invention

EXAMPLE 1

GTN=glycerol trinitrate, PBW=Parts by weight
A mixture of
24.9 PBW of polyisobutylene $\overline{M}_v$=2,800,000 (commercially available as Oppanol B 150)
12.3 PBW of polyisobutylene $\overline{M}_v$=40,000 (commercially available as Oppanol B 10)
78.8 PBW of n-heptane is processed in a kneader to give a homogeneous, viscous solution.
A suspension of
51.4 PBW of a lactose/GTN trituration (10% of GTN)
22.6 PBW of an aliphatic hydrocarbon resin (softening point R+K 97° C.)
14.4 PBW of polyisobutylene $\overline{M}_v$=40,000
3.9 PBW of a 5% solution of GTN in neutral oil and
64.9 PBW of n-heptane
is prepared in a suitable mixer.

The polyisobutylene solution and the suspension are combined by means of stirring to give a self-adhesive composition which is ready for coating and has a GTN content of 3.38% by weight.

A polyethylene terephthalate film 1, which is 0.015 mm thick, aluminized, varnished on the outside and provided with an adhesion-promoting precoat, is coated with a homogeneous layer of the above self-adhesive composition. After the solvent has evaporated at room temperature, a homogeneous, tacky self-adhesive layer 2 containing active compound remains with a dry weight of about 360 g/m$^2$.

Plasters of 16 cm$^2$ in any desired shape (for example round or oval) are cut or punched from the dried web, covered with a peel-off protective film 3 and packaged in sealed sachets. The protective film here consists of a polyethylene terephthalate film which is 0.1 mm thick, aluminized and siliconized on the side in contact with the self-adhesive composition.

Comparative experiment

The nitrate-containing plasters according to the invention were tested for bio-availability of the active compound in comparison with the state of the art, on test volunteers with a sound heart (according to the invention n=6, state of the art n=5). The plasters were stuck onto their thorax and remained there for 48 hours. No detachments or skin irritations were observed. Blood samples were taken from the test subject immediately before the application of the plasters and then at intervals after the application. The blood samples were processed in the known manner, and the glycerol trinitrate content was determined by coupled gaschromatography/mass spectrometry. The table shows the measured blood levels after the application of a plaster of the invention according to Example 1, of 16 cm$^2$ size and containing 23 mg of GTN. The comparison used was a corresponding commercially available nitrate-containing plaster according to the state of the art of German Offenlegungsschrift No. 3,315,272 Example 1, with a GTN content of 17.5 mg. This plaster also had a size of 16 cm$^2$.

| Time after application (hours) | Plasma concentration with plaster of the invention according to Example 1 (pg/ml) | Plasma concentration with plaster according to German Offenlegungsschrift 3,315,272 (pg/ml) |
|---|---|---|
| 0.25 | 13 | 13 |
| 0.5 | 78 | 41 |
| 1 | 64 | 58 |
| 2 | 69 | 74 |
| 4 | 63 | 52 |
| 6 | 59 | 58 |
| 8 | 88 | 64 |
| 12 | 63 | 63 |
| 24 | 49 | 22 |
| 48 | 29 | — |

It is seen in particular that the GTN plasters according to the invention produce the desired, almost constant blood levels in the range from 12 to 24 hours and still give significant plasma concentrations of GTN even up to 48 hours. By contrast, the GTN blood levels measured after the application of nitrate-containing plasters according to the state of the art have already dropped after 24 hours to a therapeutically no longer relevant value.

We claim:
1. A self-adhesive plastic with glycerol trinitrate for transdermal administration and having a surface for directly contacting the skin of a user, comprising:
   (a) a carrier film,
   (b) a layer of glycerol-trinitrate containing self-adhesive composition of a saturated rubber and a tackifying resin, said saturated rubber comprising a high-molecular, structure-forming component and a low-molecular, plasticizing component, said layer having one surface disposed on the carrier film and having an exposed surface constituting the surface of the plaster for directly contacting the skin of a user, and
   (c) a peel-off protective film on the exposed surface of the layer and removable during use to permit said exposed surface to directly contact the skin of a user.

2. The plaster according to claim 1, wherein the saturated rubber comprises 85–40% by weight of a higher-molecular, structure-forming component having a mean molecular weight of 2,400,000–3,200,000 and 15–60% by weight of a low-molecular, plasticizing component having a mean molecular weight of 30,000–50,000.

3. The plaster according to claim 2, wherein the saturated rubber comprises 55–45% by weight of the higher-molecular, structure-forming component and 45–55% by weight of the low-molecular, plasticizing component.

4. The plaster according to claim 2 or 3, wherein the higher-molecular, structure-forming component of the saturated rubber has a mean molecular weight of 2,800,000 and the low-molecular, plasticizing component of the saturated rubber has a mean molecular weight of 40,000.

5. The plaster according to claim 1, wherein the saturated rubber is polyisobutylene.

6. The plaster according to claim 1 or 5, wherein the tackifying resin is an aliphatic hydrocarbon resin.

7. The plaster according to claim 1, wherein the self-adhesive composition contains 40–70% by weight of saturated rubber and 60–30% by weight of tackifying resin.

8. The plaster according to claim 7, wherein the self-adhesive composition contains 45–55% by weight of saturated rubber and 55–45% by weight of tackifying resin.

9. The plaster according to claim 1, wherein the glycerol trinitrate is present together with a stabilizer.

10. The plaster according to claim 9, wherein the glycerol trinitrate is present together with 90–95% by weight of lactose as the stabilizer.

11. The plaster according to claim 1, wherein the self-adhesive composition containing glycerol trinitrate is applied in a quantity of 100–500 g/m$^2$.

12. The plaster according to claim 1, wherein the self-adhesive composition containing glycerol trinitrate is applied in a quantity of 200–400 g/m$^2$.

13. The plaster according to claim 1, wherein an individual plaster of 16 cm$^2$ size contains 20–40 mg of glycerol trinitrate.

14. The plaster according to claim 1, wherein at least one of the carrier and peel-off protective film consist of an impermeable film.

15. The plaster according to claim 14, wherein the impermeable film comprises a metallized plastic film.

* * * * *